United States Patent [19]

Holick et al.

[11] 4,410,515

[45] Oct. 18, 1983

[54] VITAMIN D GLYCOSIDES AND A METHOD OF USE

[75] Inventors: Sally A. Holick; Michael F. Holick, both of Sudbury, Mass.

[73] Assignee: Massachusetts General Hospital, Boston, Mass.

[21] Appl. No.: 249,922

[22] Filed: Apr. 1, 1981

[51] Int. Cl.³ .................. C07H 15/20; C07H 15/18
[52] U.S. Cl. .................. 424/180; 536/4.1; 536/18.1; 536/17.2; 536/55.2; 536/53; 568/665; 568/817; 568/819
[58] Field of Search ............ 536/4, 17.2, 18.1, 4.1; 568/665, 817, 819; 424/180

[56] References Cited

U.S. PATENT DOCUMENTS 4,188,345 2/1980 DeLuca et al. ............... 568/665

OTHER PUBLICATIONS

Haussler et al., Life Sciences, vol. 18, pp. 1049–1056, (1976).
Wassermann et al., Science, vol. 194: 853–855, (1976).
Napoli et al., Journal of Biological Chemistry 252: 2580–2583, (1977).
Wasserman, Science 183: 1092–1094, (1974).
LeVan et al., Biochemistry 20: 222–226, (Jan. 6, 1981).
Nagubandi et al., Journal of Clinical Investigation, vol. 66: 1274–1280, (Dec. 1980).
Hughes et al., Nature, 268: 347–349, (1977).
Peterlik et al., FEBS Ltrs. 56: 16–19, (1975).
Humphreys, Nature New Biology 246: 155–157, (1973).
Peterlik et al., Biochemical and Biophysical Research Communications 70: 797–804, (1976).
Holick et al., Biochemistry 10: 2799–2804, (1971).

Uribe et al., Biochemical and Biophysical Research Communications 58: 257–262, (1974).

Primary Examiner—Johnnie R. Brown
Attorney, Agent, or Firm—Oblon, Fisher, Spivak, McClelland & Maier

[57] ABSTRACT

A synthetic compound which is biologically active in maintaining calcium and phosphorous metabolism in animals, of the formula I

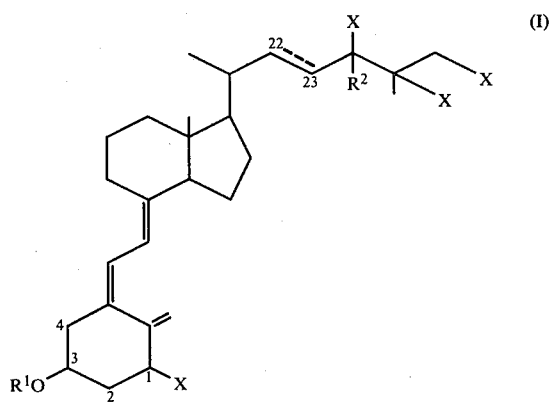

wherein the double bond between positions C-22 and C-23 is single or double; $R^2$ is hydrogen, $CH_3$ or $CH_2CH_3$; X is selected from the group consisting of hydrogen and $-OR^1$, where $R^1$ is hydrogen or a straight or branched chain glycosidic residue containing 1–20 glycosidic units per residue; with the proviso that at least one of the $R^1$ is a glycosidic residue.

19 Claims, No Drawings

VITAMIN D GLYCOSIDES AND A METHOD OF USE

BACKGROUND OF THE INVENTION

1. Field of the Invention

The present invention relates to water-soluble synthetic glycosides of vitamin D, and their use in the regulation of calcium metabolism.

2. Description of the Prior Art

Vitamin $D_3$ deficiency, or disturbances in the metabolism of vitamin $D_3$ cause such diseases as rickets, renal osteodystrophy and related bone diseases, as well as, generally, hypo- and hyper-calcemic states. Vitamin $D_3$ and its metabolites are therefore crucial in maintaining normal development of bone structure by regulating blood calcium levels.

Vitamin $D_3$ is rapidly converted to 25-OH-$D_3$ in the liver. In response to hypocalcemia, 25-OH-$D_3$, the major circulating metabolite of the vitamin, undergoes further metabolism in the kidney to $1\alpha$, 25-$(OH)_2D_3$. $1\alpha$, 25-$(OH)_2D_3$ acts more rapidly than either $D_3$ or 25-OH-$D_3$. Additionally, the dihydroxy form of the vitamin is 5-10 times more potent than $D_3$, and about 2-5 times more potent than the monohydroxy form of the vitamin, in vivo, provided it is dosed parenteraly and daily (Napoli, J. L. and Deluca, H. F., "Blood Calcium Regulators" and references cited therein in: Burger's Medicinal Chemistry, 4th Ed., part II, edited by Manfred Wolf, Wiley-Interscience, 1979, pp. 725-739).

Vitamin $D_2$, vitamin $D_3$ or their metabolites which are hydroxylated at positions 1; 1,25; 1,24,25; 24,25; 25,26; or 1,25,26 are water-insoluble compounds. When a drug is relatively insoluble in an aqueous environment or in the gastrointestinal lumen, post-administration dissolution may become the rate-limiting step in drug absorption. On the other hand, with water-soluble drugs, dissolution occurs rapidly and thus facilitates transport through the blood and to the site of activity. It would therefore be desirable to provide a form of vitamin D ($D_3$ or $D_2$) which is hydrophilic and/or water-soluble, yet preserves the normal biological properties of the water-insoluble drug.

The extracts from the leaves of a South American plant, Solanum malacoxylon (hereinafter "S.m."), have been demonstrated to contain a water-soluble principle which is different than 1,25$(OH)_2D_3$ and which, upon treatment with glycosidase enzymes yields 1,25$(OH)_2D_3$, plus a water-soluble unidentified fragment. (See, for example, Haussler, M. R., et al, Life Sciences, Volume 18: 1049-1056 (1976); Wasserman R. H., et al., Science 194: 853-855 (1976); Napoli, J. L., et al., The Journal of Biological Chemistry, 252: 2580-2583 (1977)).

A very similar water-soluble principle, which upon treatment with glycosidases also yields 1,25 dihydroxy vitamin $D_3$, is found in the plant Cestrum diurnum (hereinafter "C.d."); Hughes, M. R., et al., Nature, 268: 347-349 (1977)). The water soluble extracts from S.m. or C.d. have biological activity which is similar to that of $1\alpha$, 25-dihydroxy vitamin $D_3$.

The only evidence existing to date concerning the structure of the water-soluble fragment released during glycosidase treatment of the water-soluble principles from these plants is indefinite. The authors of the aforementioned publications have concluded that the structure is probably a glycoside, on the basis of enzymatic evidence, the water-solubility, and the use of chemical detection reagents (Peterlik, N. and Wasserman, R. H., FEBS Lett. 56: 16-19 (1973)). Humphreys (Nature (London) New Biology 246: 155 (1973)), however, has cast some doubt on this conclusion since he demonstrated that the Molisch carbohydrate test was negative for the principle.

Since it is known that the molecular weight of the water-soluble vitamin $D_3$-containing principle, prior to enzymatic release, is considerably greater than 1000 (Humphreys, D. J., Nature (London) New Biology 246: 155 (1973)), the molecular weight of the water-soluble conjugated fragment released by enzymatic hydrolysis can be calculated to be considerably greater than 584, the molecular weight of dihydroxy vitamin $D_3$ being 416. Thus, if the water-soluble fragment released by enzymatic hydrolysis were in fact a glycoside, it would contain more than 3 glycosidic (glycopyranosyl or glycofuranosyl) units.

Moreover, the results of enzymatic release are fully consistent with a wide variety of structures. For example, Haussler, M. R., et al., Life Sciences 18: 1049-1056 (1976) disclose the use of mixed glycosidases derived from Charonia lampus to hydrolyze the water-soluble principle. This enzyme is really a mixture of enzymes, as follows (Miles Laboratories, 1977 Catalog): $\beta$-glucosidase (11 units), $\alpha$-mannosidase (33 units), $\beta$-mannosidase (5.2 units), $\alpha$-glucosidase (4.8 units), $\beta$-galactosidase (44 units), $\alpha$-galactosidase (26 units), $\alpha$-fucosidase (24 units), $\beta$-xylosidase (8.2 units), $\beta$-N-acetylglucosaminidase (210 units), $\alpha$-N-acetylgalactosaminidase (41 units), and $\beta$-N-acetylgalactosaminidase (25 units). Peterlik, M., et al. (Biochemical and Biophysical Research Communications, 70: 797-804 (1976)) in their study of the S.m. extract with $\beta$-glucosidase (almond) from Sigma Chemical Company, utilized an enzyme that also contained $\beta$-D-galactosidase, and $\alpha$-D-mannosidase activities (Sigma Chemical Company, February 1981 Catalog; see also, Schwartz, J., et al., Archives of Biochemistry and Biophysics, 137: 122-127 (1970)).

In sum, the results observed by these authors are consistent with a wide range of structures, none of which have been well characterized but which, even if proven to be glycosides, contain at least more than 3 glycosidic units per vitamin D unit.

A need, therefore, continues to exist for a well-defined, well-characterized water-soluble form of vitamin D, which will be hypocalcemically active and maintain calcium and phosphorus homeostasis.

SUMMARY OF THE INVENTION

It is therefore an object of the invention to provide well characterized, well defined synthetic, water-soluble forms of vitamin $D_3$, vitamin $D_2$, and hydroxylated metabolites thereof.

It is another object of the invention to provide water-soluble forms of the aforementioned vitamins D which are hypocalcemically active, and which are active in maintaining calcium and phosphorous homeostasis in the animal body.

Still another object of the invention is to provide a pharmaceutical composition containing the aforementioned vitamins.

Yet another object of the invention is to provide a method for the treatment of hypocalcemia, and calcium and phosphorous metabolic disorders in animals, by using the aforementioned water-soluble forms of vitamin D.

These and other objects of the invention, as will hereinafter become more readily apparent, have been attained by providing:

A synthetic compound which is biologically active in maintaining calcium and phosphorous homeostasis in animals, of the formula (I)

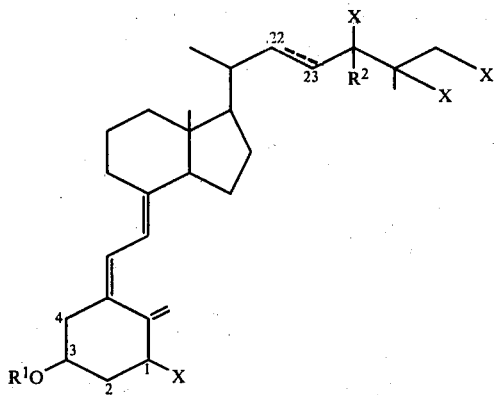

wherein
the bond between carbons C-22 and C-23 is single or double; $R^2$ is hydrogen, —$CH_3$ or —$CH_2CH_3$;
wherein X is selected from the group consisting of hydrogen and —$OR^1$, where $R^1$ is hydrogen or a straight or branched chain glycosidic residue containing 1–20 glycoside units per residue; with the proviso that at least one of said $R^1$ is a glycosidic residue.

DESCRIPTION OF THE PREFERRED EMBODIMENTS

The present invention provides for the first time well defined and substantially pure characterized synthetic, water-soluble forms of vitamins $D_3$ and $D_2$, as well as hydroxylated derivatives of these vitamins. The compounds of the present invention may in many instances be crystalline. They represent a distinct advance over the partially purified, poorly characterized presumed "glycoside" of 1α, 25-dihydroxy vitamin $D_3$ of the prior art.

The compounds of the invention are those having the formula (I):

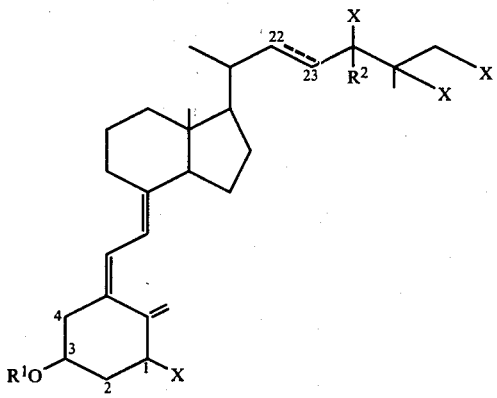

wherein
the bond between carbons C-22 and C-23 is single or double; $R^2$ is hydrogen, —$CH_3$ or —$CH_2CH_3$;
wherein X is selected from the group consisting of hydrogen and —$OR^1$, where $R^1$ is hydrogen or a straight or branched chain glycosidic residue containing 1–20 glycoside units per residue;
with the proviso that at least one of said $R^1$ is a glycosidic residue.

By glycosidic units are meant glycopyranosyl or glycofuranosyl, as well as their amino sugar derivatives. The residues may be homopolymers, random, or alternating or block copolymers thereof. The glycosidic units have free hydroxy groups, or hydroxy groups acylated with a group

wherein $R^3$ is hydrogen, lower alkyl, aryl or aralkyl. Preferably $R^3$ is $C_1$–$C_6$ alkyl, most preferably acetyl or propionyl; phenyl, nitrophenyl, halophenyl, lower alkyl-substituted phenyl, lower alkoxy substituted phenyl, and the like; or benzyl, nitrobenzyl, halobenzyl, lower alkyl-substituted benzyl, lower alkoxy-substituted benzyl, and the like.

When the compounds of formula (I) have a double bond at position C-22, they are derivatives of vitamin $D_2$, whereas if the bond at that position is single, and there is a lack of a $C_{24}$ alkyl they are derivatives of vitamin $D_3$. The latter are preferred.

The compounds of the invention contain at least one glycosidic residue at positions 1, 3, 24, 25 or 26. They may, however, contain more than one, and up to five such glycosidic residues simultaneously.

Preferred are those compounds derived from vitamins $D_3$ or $D_2$; 1-hydroxy-vitamins $D_3$ or $D_2$; 1, 25-dihydroxy vitamins $D_3$ or $D_2$; 24, 25-dihydroxy-vitamins $D_3$ or $D_2$; 25, 26-dihydroxy vitamins $D_3$ or $D_2$; 1, 24, 25-trihydroxy vitamins $D_3$ or $D_2$ and 1,25,26-trihydroxy-vitamins $D_3$, or $D_2$. Most preferred among these are vitamins $D_3$ or $D_2$; 1-hydroxy-vitamins $D_3$ or $D_2$; and 1,25 dihydroxy-vitamins-$D_3$ or $D_2$.

In the case of multihydroxylated forms of the vitamins (e.g.: 1,25-dihydroxy-vitamin $D_3$ has three hydroxy groups, at positions 1, 3 and 25), the preferred compounds of the invention are those wherein less than all of the multiple hydroxy groups are glycosilated, most preferably those where only one of the multiple hydroxy groups is glycosilated.

The glycosides can comprise up to 20 glycosidic units. Preferred, however, are those having less than 10, most preferred, those having 3 or less than 3 glycosidic units. Specific examples are those containing 1 or 2 glycosidic units in the glycoside residue.

The glycopyranose or glycofuranose rings or amino derivatives thereof may be fully or partially acylated or completely deacylated. The completely or partially acylated glycosides are useful as defined intermediates for the synthesis of the deacylated materials.

Among the possible glycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, N- acetylneuraminic acid, D-glucosamine, lyxosylamine, D-galactosamine, and the like.

When more than one glycosidic unit is present on a single hydroxy group (i.e., di or polyglycosidic residues), the individual glycosidic rings may be bonded by 1-1, 1-2, 1-3, 1-4, 1-5 or 1-6 bonds, most preferably 1-2, 1-4 and 1-6. The linkages between individual glycosidic rings may be α or β.

The configuration of the oxygen linkage of a hydroxy group, or glycosidic residue attached to the vitamin $D_3$ or $D_2$ molecule may be either α (out of the plane of the paper) or β (into the plane of the paper). It is preferred if the configuration of the 3-hydroxy or glycosidoxy group at C-3 be β, and that, independently or simultaneously the configuration of the hydroxy or glycosidoxy at C-1 be α. It is also preferred that the configuration around C-24 be R. When, at C-24, X=H and $R^2$=—$CH_3$ or —$CH_2CH_3$ the configuration at C-24 is preferably S.

Specific examples of compounds of the invention are:
vitamin $D_3$, 3β-(β-D-glucopyranoside);
vitamin $D_3$, 3β-(β-D-fructofuranoside);
vitamin $D_3$, 3β-(β-cellobioside);
vitamin $D_3$, 3β-(β-maltoside);
vitamin $D_3$, 3β-(β-lactoside);
vitamin $D_3$, 3β-(β-trehaloside);
vitamin $D_3$, 3β-raffinoside;
vitamin $D_3$, 3β-gentiobioside;
1α-hydroxy-vitamin $D_3$, 3β-(β-D-glucopyranoside);
1α-hydroxy-vitamin $D_3$, 3β-(β-D-fructofuranoside);
1α-hydroxy-vitamin $D_3$, 3β-(β-cellobioside);
1α-hydroxy-3β-(β-maltosyl) vitamin $D_3$;
1α-hydroxy-3β-raffinosyl-vitamin $D_3$;
1α-hydroxy-3β-gentiobiosyl-vitamin $D_3$;
1α-(β-D-glucopyranosyl)-vitamin $D_3$;
1α-(β-D-fructofuranosyl)-vitamin $D_3$;
1α-(β-cellobiosyl)-vitamin $D_3$;
1α-(β-maltosyl)-vitamin $D_3$;
1α-(β-lactosyl) vitamin $D_3$;
1α-(β-trehalosyl)-vitamin $D_3$;
1α-raffinosyl-vitamin $D_3$;
1α-gentiobiosyl-vitamin $D_3$;
1α, 25-dihydroxy-vitamin $D_3$, 3β-(β-D-fructofuranoside)
1α, 25-dihydroxy vitamin $D_3$, 3β-(β-D-glucopyranoside);
1α-(β-D-glycopyranosyl)-25-hydroxy-vitamin $D_3$;
1α-(β-D-fructofuranosyl)-25-hydroxy-vitamin $D_3$;
1α-hydroxy-25(β-D-fructofuranosyl)-vitamin $D_3$;
1α-hydroxy, 25-(β-cellobiosyl)-vitamin $D_3$;
1α-hydroxy, 25-(β-maltosyl)-vitamin $D_3$;
1α-hydroxy, 25-(β-lactosyl)-vitamin $D_3$;
1α-hydroxy, 25-(β-trehalosyl-vitamin $D_3$;
1α-hydroxy, 25-raffinosyl-vitamin $D_3$;
1α-hydroxy, 25-gentiobisyl-vitamin $D_3$.

All of the aforementioned derivatives can also be prepared with vitamin $D_2$.

The glycosidic derivatives of vitamins D of the present invention can be prepared by standard synthetic methods well known to those skilled in the art. These methods depend on whether the starting vitamin $D_3$ or vitamin $D_2$ contains one or more hydroxy groups. When the vitamin contains only one hydroxy group, the syntheses are straightforward, since the monohydroxylated vitamin D (hydroxylated at position 3) is treated with silver carbonate in a refluxing solution of an inert nonpolar solvent such as benzene or toluene, to which is added a fully acylated glycoside or fully acylated straight or branched chain glycosidic polymer, either of these containing an appropriate leaving group (L.G.) at position C-1' of the terminal ring (or on the single ring, as called for). Condensation occurs according to the following reaction, indicated here for a single glycoside for purpose of illustration only:

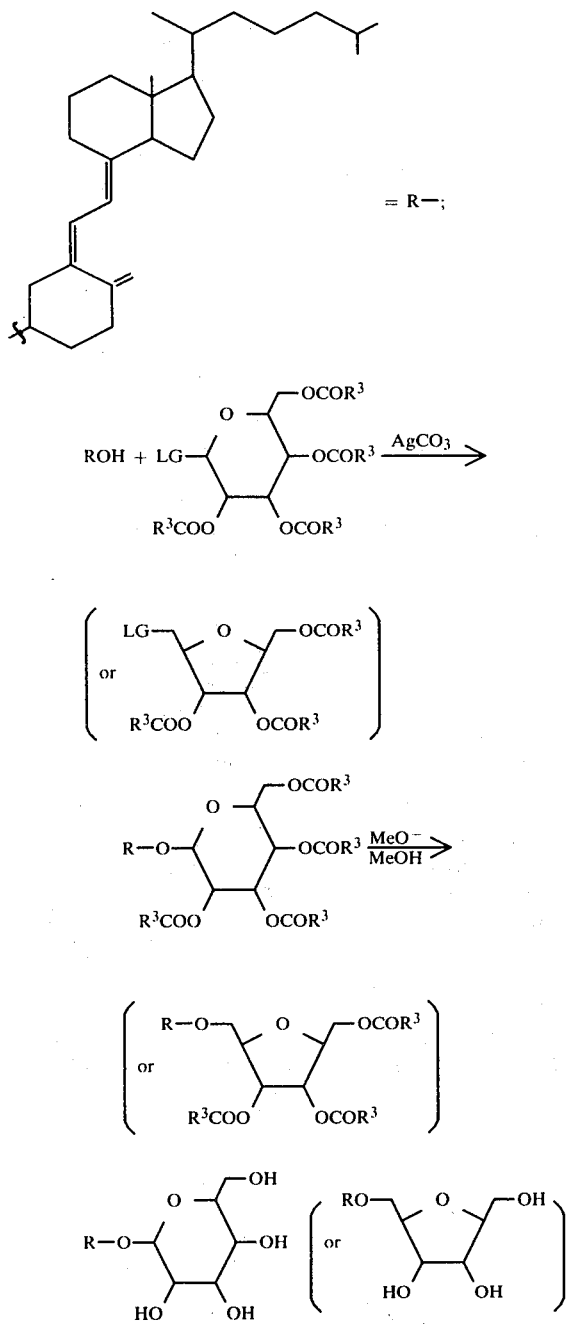

In this reaction sequence, $R^3$ is as defined previously, LG is a common leaving group such as bromine, chlorine, iodine, p-toluenesulfonyl, and the like, capable of being replaced in a bimolecular nucleophilic substitution reaction.

When the vitamin $D_3$ or $D_2$ is reacted with a glycosidic polymer, one or more of the $OCOR^3$ groups in the glycopyranoside or glycofuranoside rings is replaced by a fully acylated glycosidic unit, with the proviso that the total number of glycosidic units not exceed 20.

The reaction is carried out at from room temperature to refluxing conditions for a period of 1–10 hours, and is thereafter cooled and filtered to remove the silver salt. The filtrate is dried and the inert solvent is evaporated. The resulting product can be purified by any of the standard modern purification methods such as high performance liquid chromatography, silicic acid chromatography, thin layer preparative chromatography, and the like. A mixture of two products is normally obtained, being the $\alpha$ and $\beta$ glycofuranosyl or glycopyranosyl derivatives at the point of ring attachment. These can normally be separated by the aforementioned chromatographic methods.

After separation of the individual products, the glycosidic residues are deacylated in base, such as sodium methoxide in methanol, or ammonia in methanol. Further purification by high performance chromatography is usually indicated to obtain the highly purified product.

When the starting vitamin D ($D_3$ or $D_2$) carries two hydroxy groups (such as in 1-hydroxy vitamin $D_3$, or 25-hydroxy vitamin $D_3$) one of these needs to be selectively protected with a protecting group which can be ultimately removed after the condensation, and before, during or after the deacylation of the glycosidic residues. The same is true if three or more hydroxy groups are present in the vitamin starting materials, and less than all of these require to be glycosylated.

The selective protection of hydroxy groups in the starting materials can be carried out by using standard protection and deprotection reactions, well known to those skilled in Organic Chemistry.

Because each of the hydroxyl groups on the vitamin D molecule have different reactivities either due to the fact that they are either primary (eg. 26-OH), secondary (eg. 24-OH, $3\beta$-OH, etc.) or tertiary (eg. 25-OH) hydroxyl functions, selectivity can be achieved. Furthermore, because of steric considerations the $3\beta$-OH has different reactivity than the $1\alpha$-OH which is both a vicinyl hydroxyl function as well as sterically hindered by the exocyclic $C_{19}$ methylene function on $C_{10}$. A good example of these reactivities is illustrated in Holick et al., Biochemistry: 10, 2799, 1971, where it is shown that the trimethylsilyl ether derivative of 1,25-$(OH)_2$-$D_3$ can be hydrolyzed in HCl-MeOH under mild conditions to yield 3,25-disilyl ether, and 25-monosilyl ether derivatives of 1,25-$(OH)_2$-$D_3$. Furthermore, to obtain a 1,25-$(OH)_2$-$D_3$ whereby the 3 and 1 hydroxyls are protected, the 25-monosilyl ether derivative of 1,25-$(OH)_2$-$D_3$ can be acetylated to form the 1,25-$(OH)_2$-$D_3$-1,3-diacetyl-25-trimethyl silyl ether. Because the acetates are quite stable to acid hydrolysis, this derivative can be acid hydrolyzed to yield 1,3-diacetoxy-25-hydroxyvitamin $D_3$. An alternative approach would simply be to acetylate 1,25-$(OH)_2$-$D_3$ in acetic anhydride in pyridine at room temperature for 24 to 48 h to yield 1,3-diacetoxy-25-hydroxyvitamin $D_3$.

For protecting the 25-hydroxyl group for 25-hydroxyvitamin $D_3$ the following can be done: 25-OH-$D_3$ can be completely acetylated in acetic anhydride and pyridine under refluxing conditions for 24 h. The 3-Ac can be selectively removed by saponification (KOH in 95% MeOH-water) at room temperature for 12 h.

Once the desired protected vitamin D derivative is prepared, the same is reacted with silver carbonate or other methods for coupling (as described eg. by Igarashi, K., in "Advances in Carbohydrate Chemistry and Biochemistry," Vol 34, 243–283, or Warren, C. D. et al., Carbohydrate Research, 82: 71–83 (1980), and the glycosidic or polyglycosidic residue as in scheme I above, followed by deacylation, deprotection and purification. Among the starting vitamin D derivatives which are readily available, are, for example:

Vitamin $D_3$;
Vitamin $D_2$;
1-hydroxy-Vitamin $D_3$;
1-hydroxy-Vitamin $D_2$;
25-OH-Vitamin $D_3$;
25-OH-Vitamin $D_2$;
1,24-$(OH)_2$-Vitamin $D_3$;
1,25-dihydroxy-Vitamin $D_3$;
1,25-dihydroxy-Vitamin $D_2$;
24,25-dihydroxy-Vitamin $D_3$;
25,26-dihydroxy-Vitamin $D_3$;
24,25-dihydroxy-Vitamin $D_2$;
1,24,25-trihydroxy-Vitamin $D_3$;
1,25,26-trihydroxy-Vitamin $D_3$;

Some materials, such as 25,26-Vitamin $D_2$, 1,24,25-trihydroxy Vitamin $D_2$ or 1,25,26-trihydroxy Vitamin $D_2$ have not yet been fully identified in the art, but can nevertheless be used if synthetically prepared.

The acylated glycoside containing a leaving group at position C-1' of the first (or only) glycosidic ring can be prepared, for example, by the methods of Fletcher, H. G., Jr., "Methods in Carbohydrate Chemistry" 2: 228 (1963), or Bonner, W. A., Journal of Organic Chemistry 26: 908–911 (1961), or Lemieux, R. U. "Methods in Carbohydrate Chemistry", Vol. II, 221–222.

Oligosacchacide intermediates can be prepared, for example, by the methods of Lemieux, R. U., J. of Amer. Chem. Soc. 97: 4063–4069 (1975); or Frechet, J. M. J., "Polymer-Supported Reactions in Organic Synthesis" (1980) 407–434, or Kennedy, J. F., "Carbohydrate Chemistry" 7: 496–585 (1975).

Commercially available sugars include (Pfanstiehl Laboratories, Inc): Pentoses, such as: D-Arabinose, L-Arabinose, D-Lyxose, L-Lyxose, D-Ribose, D-Xylose, L-Xylose; Hexoses, such as: Dextroses, D-Fructose, D-Galactose, $\alpha$-D-Glucose, $\beta$-D-Glucose, L-Glucose, Levulose, D-Mannose, L-Mannose, L-Sorbose; Heptoses, such as: D-Glucoheptose, D-Mannoheptulose, Sedoheptulosan; Dissaccharides, such as: Cellobiose, 3-O-$\beta$-D-Galactopyranosyl-D-arabinose, Gentiobiose, Lactoses, $\alpha$-Lactulose, Maltose, $\alpha$-Melibiose, Sucrose, Trehalose, Turanose; Trisaccharides, such as: Melezitose, Raffinose; Tetrasaccharides, such as: Stachyose; Polysaccharides and derivatives, such as: Arabic Acid, Chitin, Chitosan, Dextrin, Cyclo-Dextrins, Glycogen, Inulin.

Alternatively, the whole synthetic sequence (protection, condensation and deprotection) can be carried out starting with a $\Delta^{5,7}$ steroidal diene which is a provitamin D. After glycosylation, the provitamin is ring-opened photochemically, and the resulting previtamin is thermally rearranged to yield glycosilated vitamin.

It is known (Napoli, J. L. and DeLuca, H. F., in "Burger's Medicinal Chemistry" 4th Ed., part II, page 728 ff) that the active form of vitamin D is 1,25-dihydroxy-vitamin $D_3$. When 1,25-dihydroxy-vitamin $D_3$ glycoside is used in the treatment of hypocalcemic states, or in the regulation of phosphorus and calcium metabolism in an animal, especially in a human, the endogenous glycosidase enzymes of the animal directly release the active form of the vitamin. On the other hand, when non-hydroxylated derivatives of the vitamin are used (such as, e.g., vitamin $D_3$ glycoside), enzymatic release of the hydroxylated vitamin is followed by hydroxylation in the liver and then in the kidney in order to form the active 1,25 dihydroxy vitamin.

The water-soluble glycosilated vitamin D conjugates of the present invention include hydrophilic derivatives of good water solubility to derivatives of excellent water solubility. They can be used generally in any application where the use of vitamin $D_3$, vitamin $D_2$ or hydroxylated derivatives thereof has been called for in the prior art. The advantage of the conjugates of the invention residue in their water-solubility and thus their ease of administration in aqueous media such as, for example, saline or aqueous buffers. This allows the utilization of these conjugates in such devices as vitamin D releasing in-line pumps, intravenous dispensation and the like. Other advantages include treatment of fat malabsorption syndromes, as well as release of the biologically active form of Vitamin $D_3$ in the gut, e.g. 1,25-$(OH)_2$-$D_3$glycoside→gut→1,25$(OH)_2$-$D_3$→biological action.

The conjugates of the invention can be administered by any means that effect the regulation of calcium and phosphorus homeostasis and metabolism in animals, especially humans. For example, administration can be topical, parenteral, subcutaneous, intradermal, intravenous, intramuscular, or interperitoneal. Alternatively or concurrently, administration can be by the oral route. The dosage administered will be dependent upon the age, health and weight of the recipient, kind of concurrent treatment if any, frequency of treatment, and the nature of the effect desired. Generally, a dosage of active ingredient compounds will be from about 0.1 $\mu$g to 1 mg per kg of body weight. Normally, from 0.1 $\mu$g to 10 $\mu$g per kg per application, in one or more applications per therapy, is effective to obtain the desired result.

An additional, unexpected property of the compounds of the invention is that some of them may demonstrate promotion of calcium absorption through the intestine without effecting calcium mobilization brought about by calcium release from bones. Calcium mobilization by bone release is a common feature of 1,25 dihydroxy vitamin $D_3$. Its selective absence in some of the compounds of the invention has a beneficial therapeutic consequence by promoting an increase in serum calcium levels by stimulating intestinal calcium transport. It is disadvantageous for patients with severe bone disease to maintain serum calcium levels at the expense of mobilizing calcium from their already wasting bones.

The compounds can be employed in dosage forms such as tablets, capsules, powder packets or liquid solutions, suspensions or elixirs for oral administration, or sterile liquids for formulations such as solutions or suspensions for parenteral use. In such compositions, the active ingredient will ordinarily always be present in an amount of at least $1 \times 10^{-6}\%$ by wt. based upon the total weight of a composition, and not more than 90% by wt. An inert pharmaceutically acceptable carrier is preferably used. Among such carriers are 95% ethanol, vegetable oils, propylene glycols, saline buffers, etc.

Having now generally described this invention, a more complete understanding can be obtained by reference to certain examples, which are included herein for purposes of illustration only and are not intended to be limiting unless otherwise specified.

EXAMPLE 1

Preparation of Vitamin $D_3$,$3\beta$-glucoside.

In a 3-neck 100-ml round-bottom flask, equipped with dropping funnel and distillation head, was suspended 1.00 g (3.63 mmole) of dry silver carbonate, freshly prepared according to the procedure of Becker, Biochem. Biophys. Act: 100: 574–581 (1965), in 5 ml of dry benzene, in which was dissolved 147 mg (0.382 mmole) of vitamin $D_3$. The solution was brought to boiling. At that point, 647 mg (1.57 mmole) of tetra-O-acetyl-$\beta$-D-glucopyranosyl bromide, prepared according to the procedure of Lemieux, supra, dissolved in 25 ml of benzene, was added drop-by-drop. Benzene continued to distill, and about $\frac{1}{2}$ hour later more silver carbonate (approximately 1 g) was added to the reaction mixture. The reaction was followed by thin layer chromatography (20:80 v/v ethyl acetate/hexane). The minor product had an $R_f$ of 0.24, and the major product had an $R_f$ of 0.20. After two hours, the reaction mixture was cooled and then filtered through glass wool to remove the silver salt. The filtrate was dried over anhydrous sodium sulfate, and the benzene was evaporated under nitrogen. The resulting yellow oil was applied to a preparative $\mu$-Porasil high-pressure liquid chromatographic column (dimensions, 8 mm $\times$ 30 cm; flow rate: 2 ml/min; solvent 15/85 v/v ethyl acetate/hexane). The major product, 9,10-secocholesta-5,7,10(19)-trien-$3\beta$-yl-2',3',4',6'-tetra-O-acetyl-$\beta$-D-glucopyranoside, with a retention time of 58 minutes exhibited an absorbance maximum of 265 nm, and an absorbance minimum of 228 nm, characteristic of the triene chromophore in vitamin D. Its mass spectrum contains a peak for the parent molecular ion and at m/e 714, 2.5% ($M^+$); peaks at 383, 5% (M-pyronium ion); 366, 28% (M-pyronium ion-water)$^+$; 351, 18%; 331, 15% (pyronium ion)$^+$; 271, 2.5%; 253, 14%; 169, 100%; $(C_8H_9O_4)^+$; 109, 63% $(C_6H_5O_2)^+$; and 60, 20% (methyl formate or acetic acid). A minor product, 9,10-secocholesta-5,7,10(19)-triene-$3\beta$-yl-2',3',4',6',-tetra-O-acetyl-$\alpha$-D-glucopyranoside with a retention time of 45 minutes, also exhibited an absorbance maximum at 265 nm and an absorbance minimum at 228 nm. Its mass spectrum exhibited a molecular ion of m/e 714.

The major product, having the retention time of 58 minutes, was then deacylated with sodium methoxide and methanol. A small piece of sodium metal was added to the compound dissolved in anhydrous methanol. After $\frac{1}{2}$ hour the solution was neutralized with dilute acetic acid. The solution was dried under nitrogen and then applied to a reverse-phase high-pressure liquid chromatographic column (Radial Pak A column Waters Associates, dimensions 0.8 $\times$ 10 cm; flow rate 1 ml/min; solvent, 98/2 v/v methanol/water). The product, 9,10-secocholesta-5,7,10(19)triene-$3\beta$-yl-$\beta$-D-glucopyranoside, had a retention time of 12.5 minutes and exhibited the UV spectrum, $\lambda_{max}$ 265 nm, $\lambda_{min}$ 228 nm, typical of the vitamin D chromophore.

The vitamin $D_3$,$3\beta$-glucoside vitamin $D_3$,$3\alpha$-glucoside and the vitamin $D_3$,$3\beta$ glucoside acetate were tested for biological activity. Male weanling rats from Holtzmann Company, Madison, Wis., U.S.A., were fed a vitamin D deficient diet that was adequate in phosphorus and low in calcium (0.02%) for $3\frac{1}{2}$ weeks. Groups of five animals received orally either 4 $\mu$g, 1 $\mu$g, 0.5 $\mu$g. 0.25 $\mu$g of Vitamin $D_3$-$3\beta$-glucoside, 1 $\mu$g Vitamin $D_3$-$3\alpha$-glucoside or 2 $\mu$g Vitamin $D_3$-$3\beta$-glucoside acetate in 50 μl of 95% ethanol or vehicle alone. 24 hours later the animals were sacrificed and the small intestine and blood were collected. Intestinal calcium transport studies were performed by the everted gut sac technique, and blood was used for serum calcium determinations. The results are shown in the following table:

| Compound | I/O (inside Ca$^{45}$/ outside Ca$^{45}$) ± S.D. | Serum Calcium ± S.D. |
|---|---|---|
| 95% ethanol | 1.6 ± 0.3 | 4.3 ± 0.2 |
| 4 μg Vitamin D$_3$, 3β-glucoside | 3.9 ± 0.2 | 5.3 ± 0.2 |
| 1 μg Vitamin D$_3$, 3β-glucoside | 3.6 ± 0.3 | |
| 0.5 μg Vitamin D$_3$, 3β-glucoside | 2.5 ± 0.2 | |
| 0.25 μg Vitamin D$_3$, 3β-glucoside | 2.0 ± 0.2 | |
| 1 μg Vitamin D$_3$ 3α-glucoside | 2.0 ± 0.4 | |
| 2 μg Vitamin D$_3$ 3β-glucoside acetate | 1.7 ± 0.2 | |

The data show that the vitamin D$_3$,3β-glucoside is capable of stimulating intestinal calcium absorption, and bone calcium mobilization. The 3 α glucoside is somewhat less active, while the 3 β-acetate appears inactive.

What is claimed is:

1. A synthetic compound which is biologically active in maintaining calcium and phosphorous metabolism in animals, of the formula I:

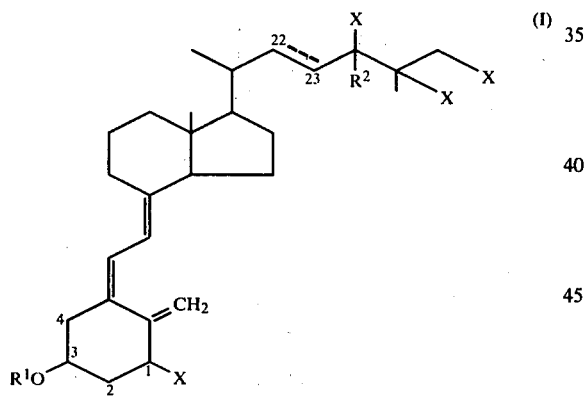

wherein
the double bond between positions C-22 and C-23 is single or double;
R$^2$ is hydrogen, methyl or ethyl;
X is selected from the group consisting of hydrogen and —OR$^1$, where R$^1$ is a glycoside selected from the group consisting of glucose, mannose, galactose, gulose, allose, altrose, idose, talose, fructose, arabinose, xylose, sucrose, cellobiose, maltose, lactose, trehalose, gentiobiose, meliobiose, raffinose, gentianose, N-acetyl-D-galactosamine, N-acetyl-D-glucosamine, N-acetyl-D-mannosamine, N-acetylneuraminic acid, D-glucosamine, lyxosylamine, and D-galactosamine, with the proviso that the total number of glycosidic units per compound is not larger than 3.

2. The compound of claim 1 wherein the bond at position C-3 is β.

3. The compound of claim 1 wherein, when X at position C-1 is —OR$^1$ wherein R$^1$ is as defined in claim 1 the bond at C-1 is α.

4. The compound of claim 1 wherein the bond between C-22 and C-23 is single, and R$^2$=H.

5. The compound of claim 1 which is

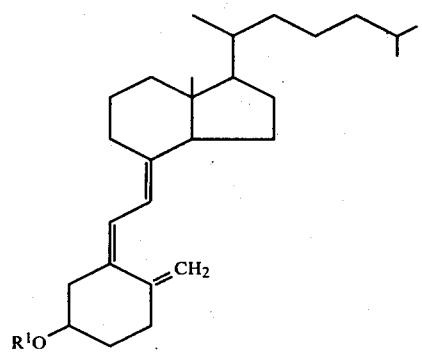

wherein R$^1$ is as defined in claim 1.

6. The compound of claim 1 which is

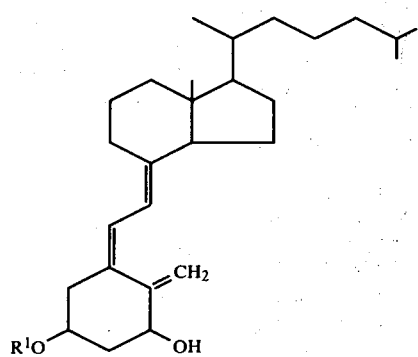

wherein R$^1$ is as defined in claim 1.

7. The compound of claim 1 which is

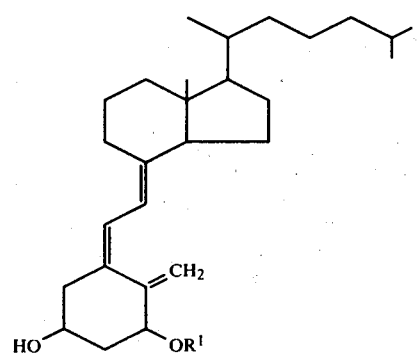

wherein R$^1$ is as defined in claim 1.

8. The compound of claim 1 which is

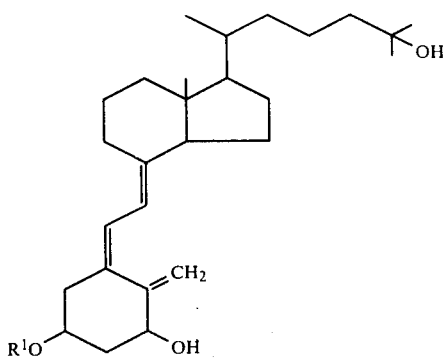

wherein R¹ is as defined in claim 1.
9. The compound of claim 1 which is

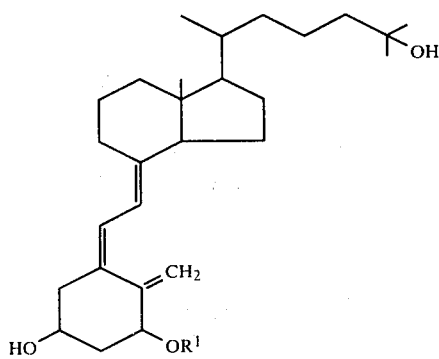

wherein R¹ is as defined in claim 1.
10. The compound of claim 1 which is

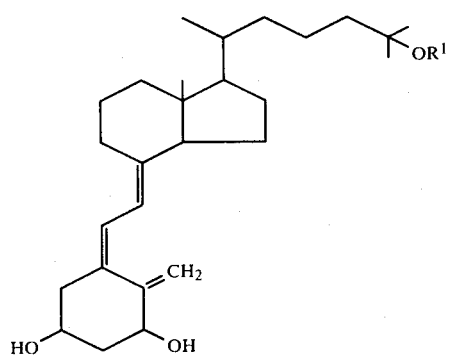

11. The compound of claim 1 which is

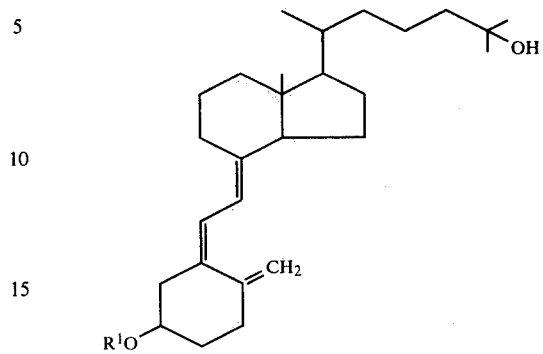

wherein R¹ is as defined in claim 1.
12. The compound of claim 1 which is

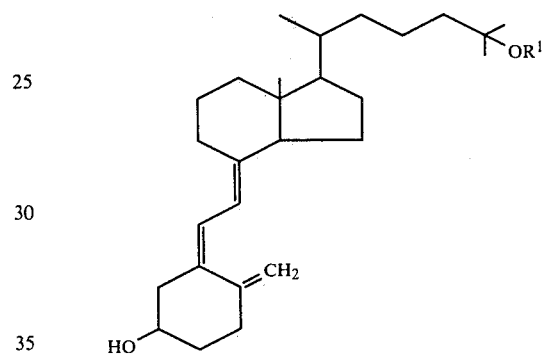

wherein R¹ is as defined in claim 1.

13. The compound of claim 1 wherein R¹ is glucose.
14. The compound of claim 13 which is vitamin D₃-3β-D-glucoside.
15. The compound of claim 13 which is 25-(glucoside)-vitamin D₃.
16. The compound of claim 13 which is 1,25-dihydroxy Vitamin D₃-3β-glucoside.
17. The compound of claim 13 which is 25-hydroxy-Vitamin D₃-3β-glucoside.
18. The compound of claim 13 which is 1-hydroxy-25-glucoside-Vitamin D₃.
19. A method of treating calcium metabolic disorders in an animal which comprises administering to said animal an amount sufficient to regulate calcium and phosphorous homeostasis in said animal, of a compound of any of claims 1, 13, 14 or 15.

* * * * *

UNITED STATES PATENT AND TRADEMARK OFFICE
CERTIFICATE OF CORRECTION

PATENT NO. : 4,410,515

DATED : October 18, 1983

INVENTOR(S) : SALLY A. HOLICK et al.

It is certified that error appears in the above—identified patent and that said Letters Patent is hereby corrected as shown below:

Column 10, lines 12 and 13 should read

--tetra-O-acetyl-$\alpha$-D-glucopyranosyl--.

Signed and Sealed this

Fourteenth Day of August 1984

[SEAL]

Attest:

Attesting Officer

GERALD J. MOSSINGHOFF

Commissioner of Patents and Trademarks